US011119100B2

(12) United States Patent
Infante et al.

(10) Patent No.: US 11,119,100 B2
(45) Date of Patent: Sep. 14, 2021

(54) REAGENT STRIPS READER FOR ANALYTES MEASUREMENT IN BODY FLUIDS CONNECTED TO A SMARTPHONE WITH EMERGENCY FUNCTION

(71) Applicant: Eido Innova, Inc., Brownsville, TX (US)

(72) Inventors: Nancy Guerra Infante, Brownsville, TX (US); Carlos Francisco Bernal Velazquez, Brownsville, TX (US)

(73) Assignee: Eido Innova, Inc., Brownsville, TX (US)

( * ) Notice: Subject to any disclaimer, the term of this patent is extended or adjusted under 35 U.S.C. 154(b) by 141 days.

(21) Appl. No.: 16/164,824

(22) Filed: Oct. 19, 2018

(65) Prior Publication Data

US 2019/0302108 A1  Oct. 3, 2019

Related U.S. Application Data

(60) Provisional application No. 62/649,484, filed on Mar. 28, 2018.

(51) Int. Cl.
| | |
|---|---|
| *G01N 33/543* | (2006.01) |
| *G16H 50/50* | (2018.01) |
| *H04M 1/72412* | (2021.01) |

(52) U.S. Cl.
CPC ....... *G01N 33/54373* (2013.01); *G16H 50/50* (2018.01); *H04M 1/72412* (2021.01); *H04M 2250/02* (2013.01)

(58) Field of Classification Search
CPC .. G01N 33/54373; G01N 33/53; G01N 33/00; G01N 33/52; B29C 35/0261; B29C 65/08; B29C 65/088; B29C 65/4835; B29C 65/5028; B29C 65/5057; B29C 65/8292; B29C 66/1222; B29C 66/1226; B29C 66/472; B29C 66/474; B29C 66/5326; B29C 66/71; B29C 66/721; B29C 66/7212; B29C 66/72141; B29C 66/73941; B29C 66/81422; B29C 66/836; B29C 66/8412; B29C 66/86533; B29C 66/9121; B29C 66/91216; B29C 66/9141; B29C 66/91411; B29C 66/91951; B29C 66/951;

(Continued)

(56) References Cited

U.S. PATENT DOCUMENTS

2016/0077091 A1* 3/2016 Tyrrell ............. G01N 33/48792
436/501
2016/0349185 A1* 12/2016 Park .................... G01N 33/558
(Continued)

FOREIGN PATENT DOCUMENTS

WO WO-2017127349 A1 * 7/2017 ....... A61B 5/150358

*Primary Examiner* — Jennifer Wecker
(74) *Attorney, Agent, or Firm* — Cognition IP, P.C.; Edward Steakley

(57) ABSTRACT

A portable monitoring strip reader may include one or more light sensors for reading urine monitoring strips. The monitoring strip reader may collect light intensity information and transmit the information to an application on a portable electronic device for analysis. The application may determine concentrations of analytes and diagnose conditions or illnesses where a concentration is too high or too low. In some aspects, the application may use machine learning models such as an anomaly detection model, diagnosis model, and measurement model.

9 Claims, 8 Drawing Sheets

(58) Field of Classification Search
CPC ............ B29C 66/9512; B29C 66/9516; B29C 66/961; B29C 66/9674; B29C 73/10; B29C 73/12; B29C 73/14; B29C 73/34
See application file for complete search history.

(56) References Cited

U.S. PATENT DOCUMENTS

2017/0173262 A1* 6/2017 Veltz .................... A61B 5/0022
2019/0012553 A1* 1/2019 Maruchi ............ G06K 9/00536
2019/0385707 A1* 12/2019 Wright .................. G16H 10/40

* cited by examiner

REAGENT STRIPS READER FOR ANALYTES MEASUREMENT IN BODY FLUIDS CONNECTED TO A SMARTPHONE WITH EMERGENCY FUNCTION

CROSS-REFERENCE TO RELATED APPLICATIONS

This application claims the benefit of U.S. Provisional Patent Application No. 62/649,484, filed Mar. 28, 2018.

FIELD OF THE INVENTION

Some embodiments relate to a portable reader of analytes in urine, controlled through a mobile application previously installed on a smartphone. Such device can be used for example, by patients suffering diabetes who need to have a routine check of certain metabolites such as glucose, protein, ketones, etc. This with the purpose of preventing complications of a poorly controlled diabetes. Conversely, the reader can also be used by users who follow a low carbohydrates diet and wish to know if their bodies are in a metabolic state called ketosis, in which the body uses fat as its main source of energy.

This analytes meter can be used in healthcare to help patients to control metabolic syndromes such as diabetes, obesity or to prevent diseases like kidney failures, etc.

BACKGROUND

Testing systems for determination are commonly used to perform various types of determination tests on different types of samples. Assessment tests can be qualitative or quantitative tests in order to assess the presence, concentration or quantity of one or more analytes in a sample.

The presence of certain analytes in the body can be used as medical risk indicators, for example, glucose, ketones, cholesterol, triglycerides, hemoglobin, A1C, fructosamine, carbohydrates, tumor markers, lead, epilepsy medication, bilirubin, hepatic function markers, toxins and its metabolites, controlled substances, blood clotting factors (PT, ATPP), etc., contained in biological samples, such as blood, urine, tissues, saliva, etc.

Such diagnosis systems can include a means of sampling (such as a sample strip, card, capsule, etc.) specifically designed to react in the presence of an analyte in a sample, and a separate electronic meter, designed to interconnect with the means of analysis, with the purpose of carrying the assessment test and indicate the results to the user.

In order to carry out an assessment test, the user must obtain a mean for testing, for example, a monitoring strip, then he or she must take a sample by using a sampling device (for example, a urine container), and then place the strip in the sample container, to then be placed in the reader, the user must wait for the reader results which will be presented as a numeric reading for example.

Nonetheless, there are some issues with this type of assessment method, since oftentimes the readers are bulky; the user needs to collect all the components of this system and carry out several steps. If the user does not have all the necessary components, such as the sample, the means of testing, the assessment reader and the logbook to save the results, it is possible that the user will not be able to carry out the measurement. Some of these assessment readers already have a memory to save the results, however, they are not connected to the Internet to share the results with a doctor, nutritionist or a relative. On the other hand, some of the assessment methods that currently exist are very expensive and/or painful.

In the specific case of urine monitoring strips, they are an instrument of basic diagnosis, whose purpose is to detect during a urine routine check, some of the pathological changes which can appear in a patient's urine.

The current monitoring strips provide a fast and simple mean to carry out the chemical analysis of the urine sample, something very important to help doctors on their diagnostic procedures. This analysis covers pH, presence of protein, glucose, ketones, hemoglobin, bilirubin, urobilinogen, nitrite, leukocytes and density among others.

The process for assessment with monitoring strips is as follows: 1. Obtain a clean container for the sample; 2. Urinate within the container; 3. Place the strip in the urine; 4. Interpret the results and; 5. Wash the container. Combined with the several steps previously cited, some of the inconveniences of this method are that the smell of the patient's urine can be unpleasant to him, or the possible contact with it while manipulating the sample. To this we add the fact that the interpretation of the results in the monitoring strip is subjective, since it depends on variations in color tone of the strip which can be easily confused.

In the current market there are some reading devices such as the one described in patent KR20140007313 with title: Urine Analyzer with User Interface, but that patent's device installs in the seat of the toilet, which is cumbersome and not practical at all. And there is another as in patent: U.S. Pat. No. 7,583,382 with title: Optical Measurement Apparatus, with the difference that it installs on the seat of the toilet and embodiments herein present a more flexible and practical proposal. This system measures the optical rotation/polarization caused by glucose present in the sample through light transmittance and embodiments herein instead use enzymatic colorimetry and measures using reflectance. The system disclosed in patent: U.S. Pat. No. 7,583,382 uses an ion exchange resin, a system that generates or refills this resin, a sensor to determine when the resin needs to be refilled, a system to produce alkaline water from the toilet water, a cleansing system to clean the resin deposit with toilet water, this system has to be mounted on the toilet which probably has to be done by a technician or installer. The system does not use any means of communication, but only a controller with a digital visualization.

Such devices present different problems to which, the embodiments herein provide a specific solution according to the structure of the device and its utilization.

There also exist some portable solutions, whose main problem relies in having to manipulate the device while in the procedure of taking the sample, which can cause splashing or wetting the device with urine.

SUMMARY

In some embodiments, a portable analytes in body fluids reader with a means of fixing which allows the user to affix the device onto a wall or the toilet, in order to be hands-free during the assessment process, controlled through the mobile application previously installed on a cellular phone, where it could be used, for example, by patients with diabetes, who need to have routine checks of certain metabolites such as glucose, microalbumin and ketonic bodies, etc.; this with the purpose of preventing complications associated with a poorly controlled diabetes. The reader of the present embodiments can also be used by users who have a diet low in carbohydrates and wish to know if their bodies are in a metabolic state called ketosis, in which the body uses fat as a main source of energy.

In some embodiments, machine learning models are used to analyze the data collected from the portable analyte reader. For example, an anomaly detection model, diagnosis model, measurement model, and other machine learning models may be used in some embodiments.

DETAILED DESCRIPTION

Figure 1:
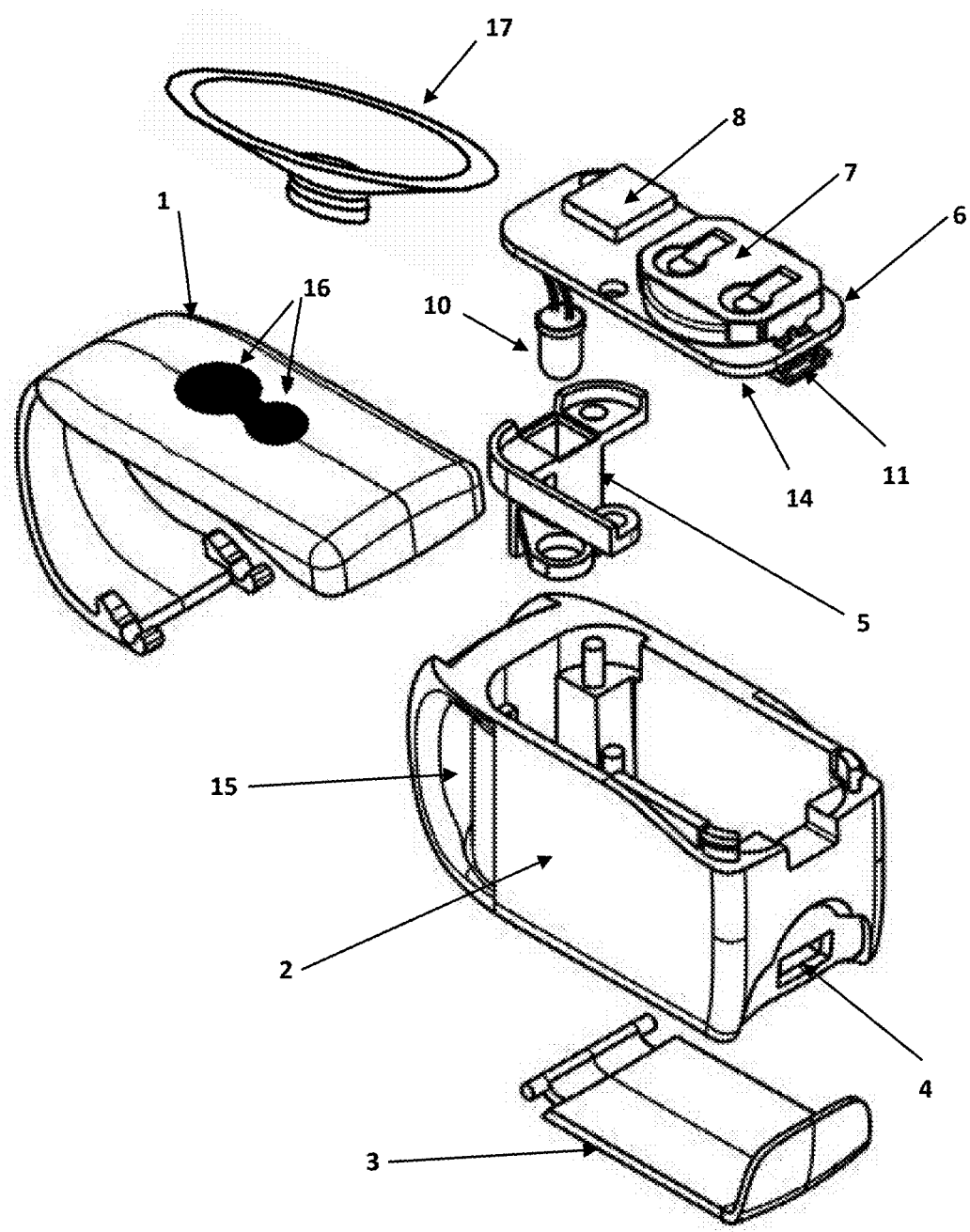
FIG. 1 illustrates the separated pieces of an exemplary strip reader from a left perspective view, seen from the backside.
Figure 2:
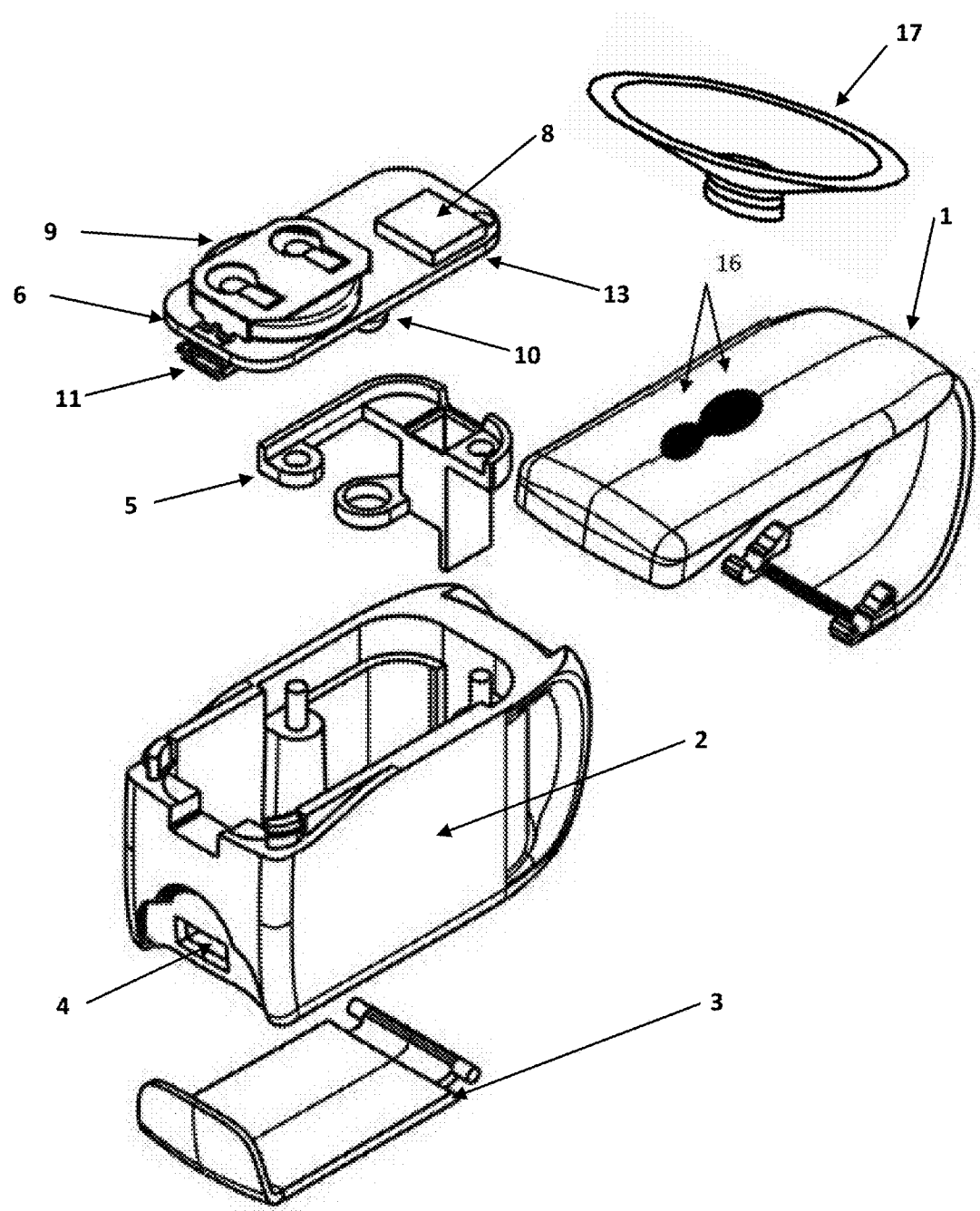
FIG. 2 illustrates the separated pieces of an exemplary strip reader from a right perspective view, seen from the backside.
Figure 2A:
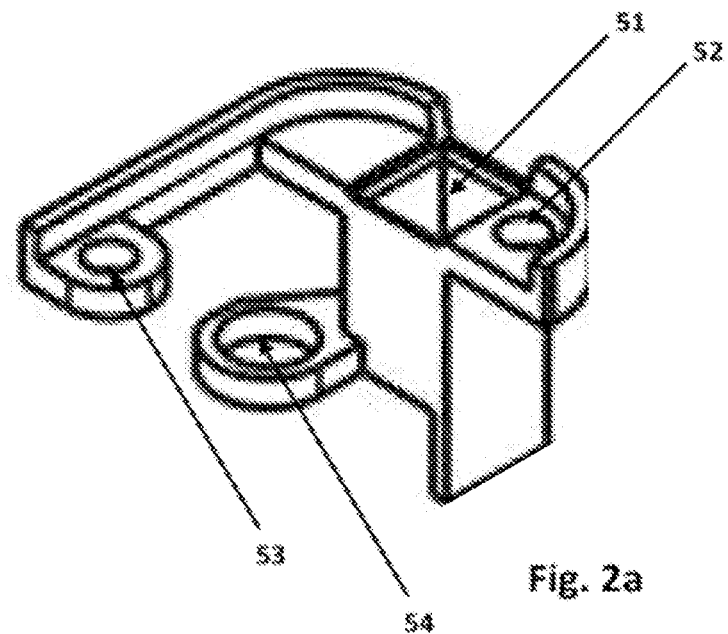
FIG. 2a illustrates an exemplary electronics' support piece that is mounted inside the main housing.
Figure 2B:
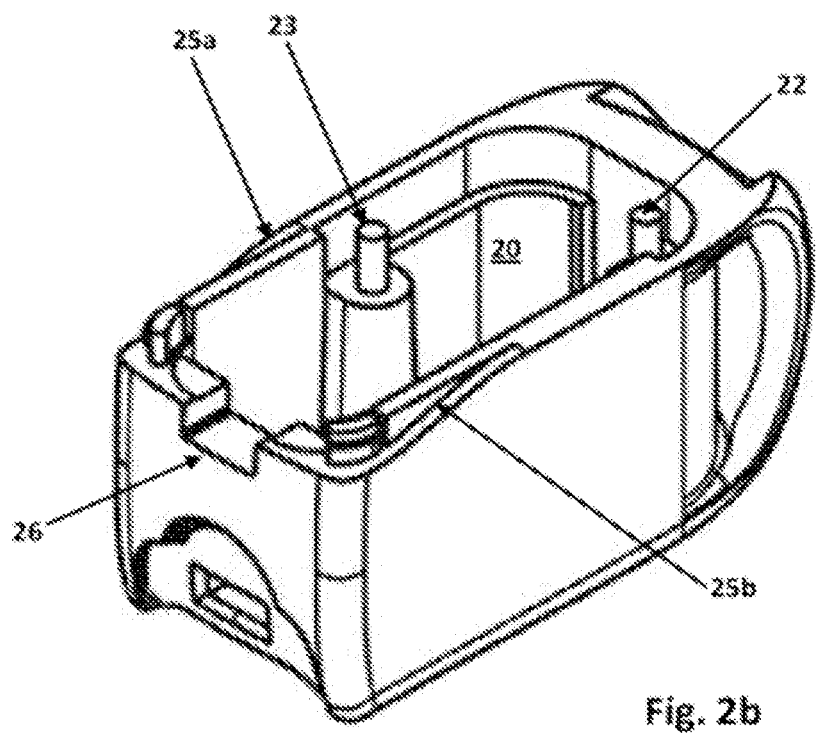
FIG. 2b illustrates an exemplary view in perspective of the main strip reader housing.
Figure 3:
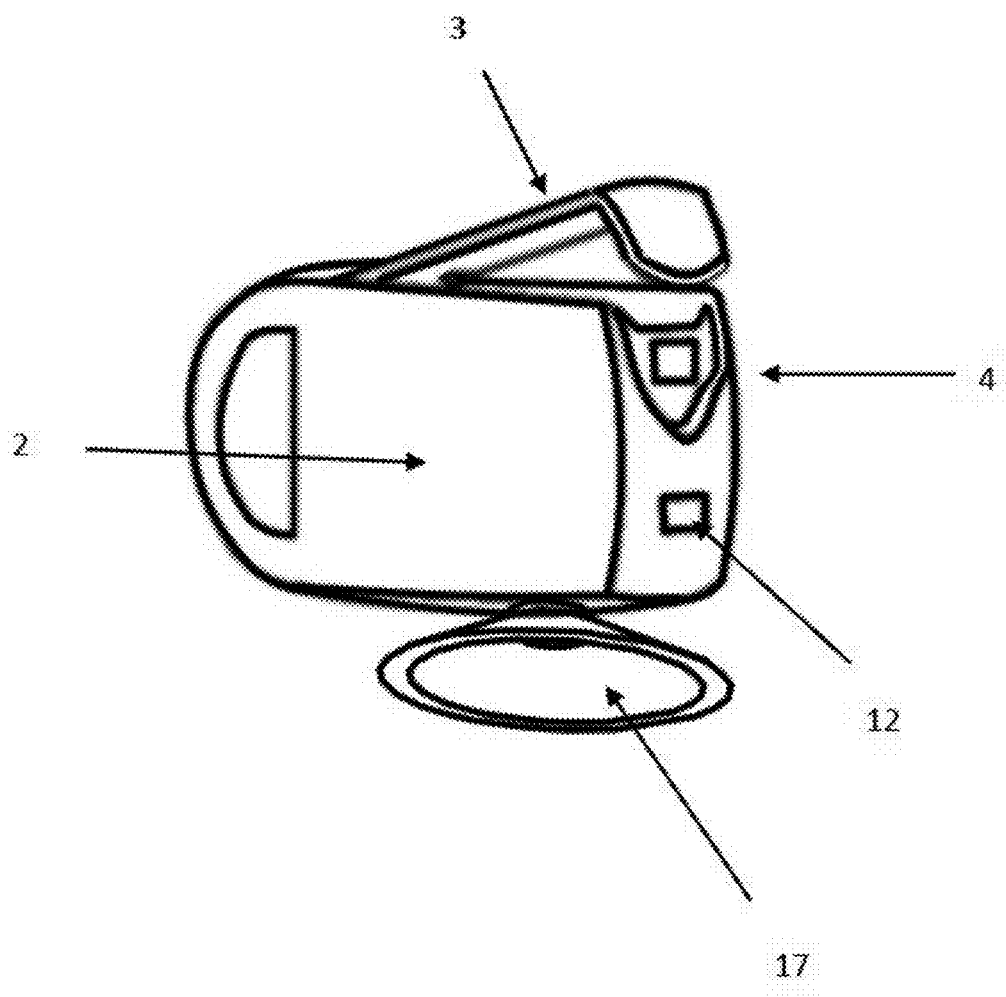
FIG. 3 illustrates an exemplary rear view of the strip reader with the suction cup installed.

One of the main components of the hands-free monitoring strip reader for the measurement of metabolites in urine connected to a smart-phone with emergency function of some embodiments, is an electronic board (6) which gathers all the electronic components: Bluetooth module (8), light sensors (10), battery (9), battery case (7) and the mini-USB connector (11) which includes a charge controller (14).

This electronic board is to be installed in a holder piece (5) which holds the LED in its position and isolates its light from the exterior light which could modify the measurement, since it is placed in a light channel (51) formed in the holders' body. The holder (5), comprises a first attachment hole (52), a second attachment hole (53), and a third attachment hole which prevents the light emitting diode from moving (54), located below in relation to the height of the first attachment hole (52) and the second attachment hole (53).

It is important to mention that the electronic board (6) was designed to hold multiple light sensors (13) and leds (10) in order to measure several metabolites simultaneously.

Once the holder (5) and the electronic board are mounted together (6), they are mounted inside a housing case (2) which embodies the whole device, such case (2) presents an upper open portion surrounded by a peripheral wall, in a first edge of the case (2) and at the border of the peripheral wall there are some longitudinal attachment clefts (25a, 25b) and between such longitudinal attachment clefts (25a, 25b) there is a mini-USB (11) connector notch receptor (26). The case (2) comprises an internal space (20) whose internal wall includes a first attachment pin (22) and a second attachment pin (23) which attaches with the first attachment hole (52) and the second attachment hole (53) respectively.

The case (2) has a cover (1) covers two thirds of the main, covering all the electronic components. The cover (1) comprises a pivotal base (1a) which has two rotary bases (1b). This cover also has two circular holes (16) in which a plastic suction cup is installed (17) which allows the user to mount the device on a wall or on the toilet, in order to be hands-free during the assessment process.

On the bottom part of the case (2), there is a cover lid (3) which gives us access to the strip container formed by a curvature on the exterior wall (20) of the case (2). The cover lid (3) also covers a strip insert opening (4) used to introduce the monitoring strips to be measured and which it is located in the first edge of the case (2) and comprises a pivotal axis (31) which attaches to the base (1a) which has two rotary bases (1b).

In some embodiments, the structural components of the strips reader and their function have a close relationship, thereby, they are specially conceived so that some embodiments provide a 'hands-free' operation method of the reader by the user, which consists in the following stages:

a) Press the button 'read' within the application of the smartphone.
b) Place the smartphone away to avoid getting it wet during the procedure.
c) Open the strip-container cover lid (3) and extract a monitoring strip from the strips' compartment (20);
d) Affix the device onto a wall, or the toilet by using the plastic suction cup (17);
e) Dampen the pouch(es) of the strip with your urine, either by placing urine in a recipient or by urinating directly over the strip.
f) Place the monitoring strip with the pouch facing front and facing up in the monitoring strips inlet hole.
g) The device receives the activation and activates the light source, once it detects the presence of the strip, it measures the light intensity in each one of the four filters (red, green, blue and with no filter)
h) The device sends the information to the installed application on the smartphone. In this stage:
Based on the received intensities and the calibration curve it calculates the concentration of the analyte to assess.
If the analyte concentration to assess is greater than the set limit, it activates the emergency functions.
The emergency functions can be sending an alert text message accompanied by the GPS location or to call a relative or an emergency number, the application could also send informational messages to the patients' physician.
Sends a message to the strip reader to activate the emergency mode.
i) If the result is out of accepted range, the device follows a preset profile by Bluetooth standards 4.0 defined in the Bluetooth module (8) as an emergency profile and starts to send periodical emergency messages, these messages can be received and identified as emergency messages by nearby Bluetooth devices.
j) Once the application on the smartphone has received the device's information, it activates a sound or vibration alert indicating it has concluded the assessment.
k) The user must extract and get rid of the monitoring strip.
l) The user must properly cleanse his hands.
m) Within the application the user presses the save button, which in turn saves the assessment result onto the user's phone as well as in the cloud database.

The following method stages are also of importance:

The user uses the smartphone-device system to assess the concentration of a certain analyte in his urine.

If the concentration of such analyte in urine is high enough to put at risk the life of the user, two procedures are then initialized:
1. The smartphone sends an alarm message or makes an emergency phone call informing that the user might need assistance. It can also provide the information of the user's location by reading the phone's GPS.
2. The device's Bluetooth module also starts an emergency procedure and sends emergency packets that can alert other nearby Bluetooth devices indicating that someone close needs assistance.

One objective of the strip reader interaction of some present embodiments and the utilization method with a phone, is to be able to use our phone's capacities instead of just saving the data onto the device; capacities such as:

The phone serves as a display, computing capacity for calculations and storage, access to the mobile network and/or WIFI and above all the easiness of updating. For example, we can go from assessing glucose to assess ketonic bodies or microalbumin with the same device, the only thing that changes is the calculation.

Another purpose of some embodiments is to be able to have a "hands-free" assessment method which seeks to avoid the user from urine splashing his assessment device or phone. Since the only thing that comes in contact with user's hands during the procedure is the monitoring strip, and then this is discarded.

Figure 4:
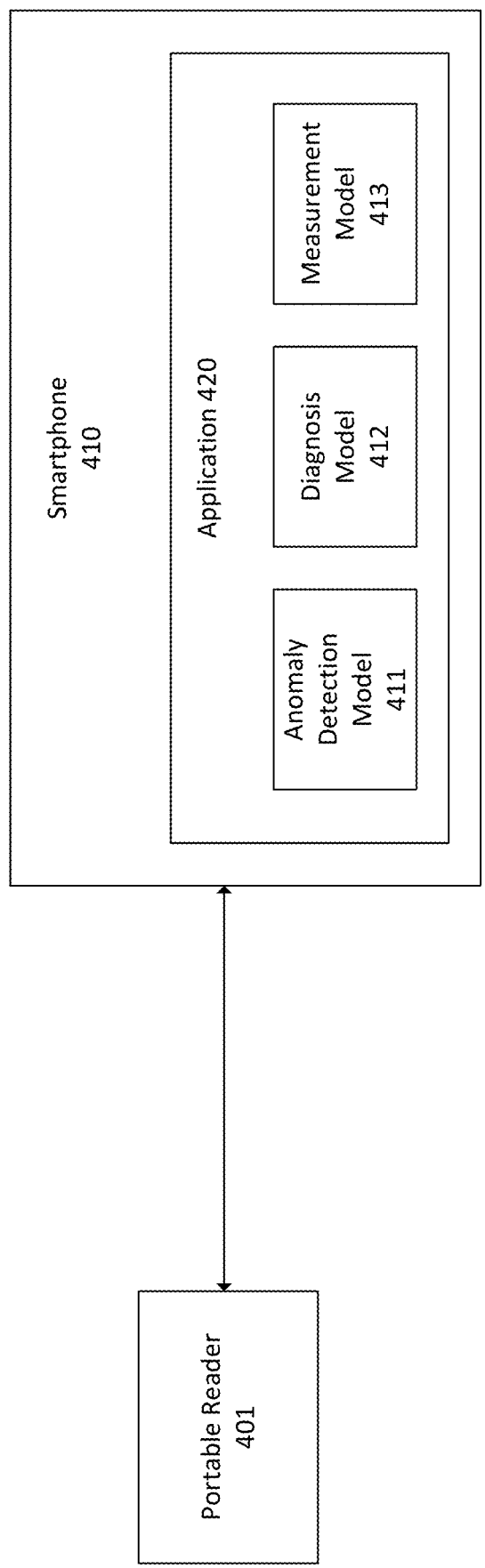
FIG. 4 illustrates the exemplary use in some embodiments of machine learning models for performing diagnosis and measurement.

FIG. 4 illustrates the exemplary use in some embodiments of machine learning models for performing diagnosis and measurement. Portable reader 401 was described herein and may comprise a reader physical separate from a smartphone for reading urine monitoring strips using light sensors. The portable reader 401 may be connected wirelessly, or by wire, with a smartphone 410. The smartphone 410 may include a software application 420 for reading and analyzing the data received from the portable reader 401. The software application 420 may include one or more machine learning models for analyzing the data, such as an anomaly detection model 411, diagnosis model 412, and a measurement model 413. Additional machine learning models may also be used in some embodiments. Machine learning may also be referred to as artificial intelligence herein.

The machine learning models may be implemented with any kind of machine learning model such as linear regression, linear classification, logistic regression, logistic classification, Naïve Bayes, Bayesian classification, decision trees, random forests, neural networks, convolutional neural networks (CNNs), recurrent neural networks (RNNs), ensemble models, or any other machine learning model or combinations of the aforementioned models.

The machine learning models may be trained using input data in the form of training examples. The training examples may include an input set of features and a target output. Through the course of training over many training examples, the machine learning model learns an association, or model, between input features and the target output. When presented with a previously unseen example comprising a set of features, the trained machine learning model may then predict the target output for the unseen example.

In some embodiments, different machine learning models 411, 412, 413 are used for different analytes. For example, a different diagnosis model 412 may be used for glucose versus ketones, and likewise for the measurement model 413. In other embodiments, the machine learning models may be the same across multiple analytes.

The machine learning models 411, 412, 413 may initially be calibrated by comparing results returned by the models to known correct analysis results returned from a reference analysis machine. A reference analysis machine may be any analyte reader that can perform analysis on analytes. The reference analysis machine may be a portable analyte reader or non-portable analyte reader. For example, a reference machine may perform diagnosis by detecting when a user is in a dangerous state due to having too many or too few of an analyte and may also measure concentrations. The machine learning models 411, 412, 413 may include tunable parameters that may be set by user, such as by setting configuration values through an options screen. The parameters may be tuned until the machine learning models 411, 412, 413 return results identical or similar to the reference machine.

Prior to performing analysis using machine learning models 411, 412, 413 the smartphone or portable reader may prompt the reader to input an indication of which test the user wants to perform. For example, the reader may prompt the user to identify the analyte or condition to test for. If the user enters a strip for the wrong analyte, which differs from the one selected, the portable reader or smartphone may display an error.

Figure 5A:
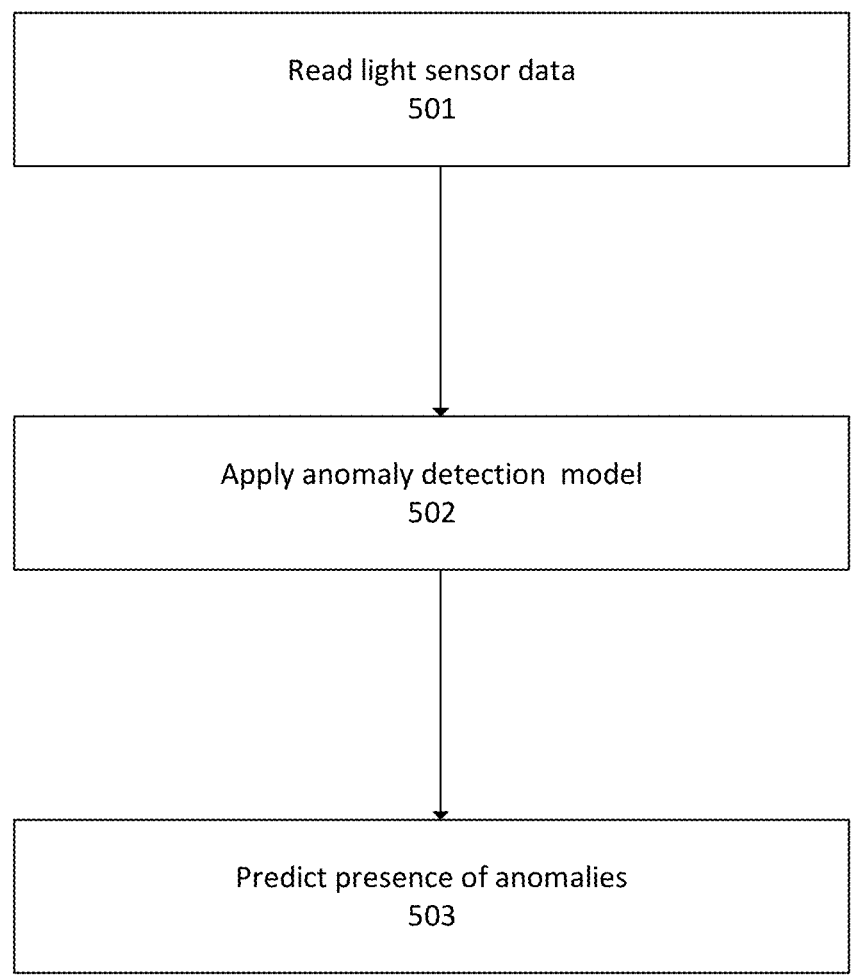
FIG. 5A illustrates an exemplary method for performing anomaly detection.

FIG. 5A illustrates an exemplary method 500 perform anomaly detection. In step 501, the portable reader 410 reads light sensor data from an inserted strip. The light sensor data may be collected from light sensors (10) and filters may be applied to collect the light data in different wavelengths such as red, green, and blue in order to generate RGB data. The RGB data may comprise intensity data for each of the colors red, green, and blue at a plurality of pixels in a two-dimensional image of the inserted strip. The portable reader 410 may transmit the RGB data to the smartphone where it may be accessed and interpreted by application 420.

In step 502, the light sensor data may be input into the anomaly detection model. The anomaly detection model may analyze the light sensor data to determine the presence of any of several conditions, including but not limited to (1) there is no strip in the device (2) the strip is not fully inserted in the device (3) the strip has expired (4) the strip is backwards or upside down (5) a strip of an incorrect type is used, such as a glucose testing strip when the user is trying to test ketones or (6) no anomaly (the strip is present and correct). The anomaly detection model may be trained to detect these conditions by inputting training examples and target outputs for the training examples. The anomaly detection model may therefore learn an association between light sensor data and the associated conditions. In one embodiment, the anomaly detection model is a classification model.

In step 503, the anomaly detection model may output a prediction of detected anomalies. The output may be a series of probabilities of the existence of each condition. The condition with highest probability may be selected as the predicted condition. In addition, the anomaly detection model may also output a confidence value that identifies the confidence with which it is making its prediction. When an anomaly is detected that would prevent correct operation, the process may stop. However, if no anomaly is detected, then the process may continue to method 510 to perform diagnosis.

Figure 5B:
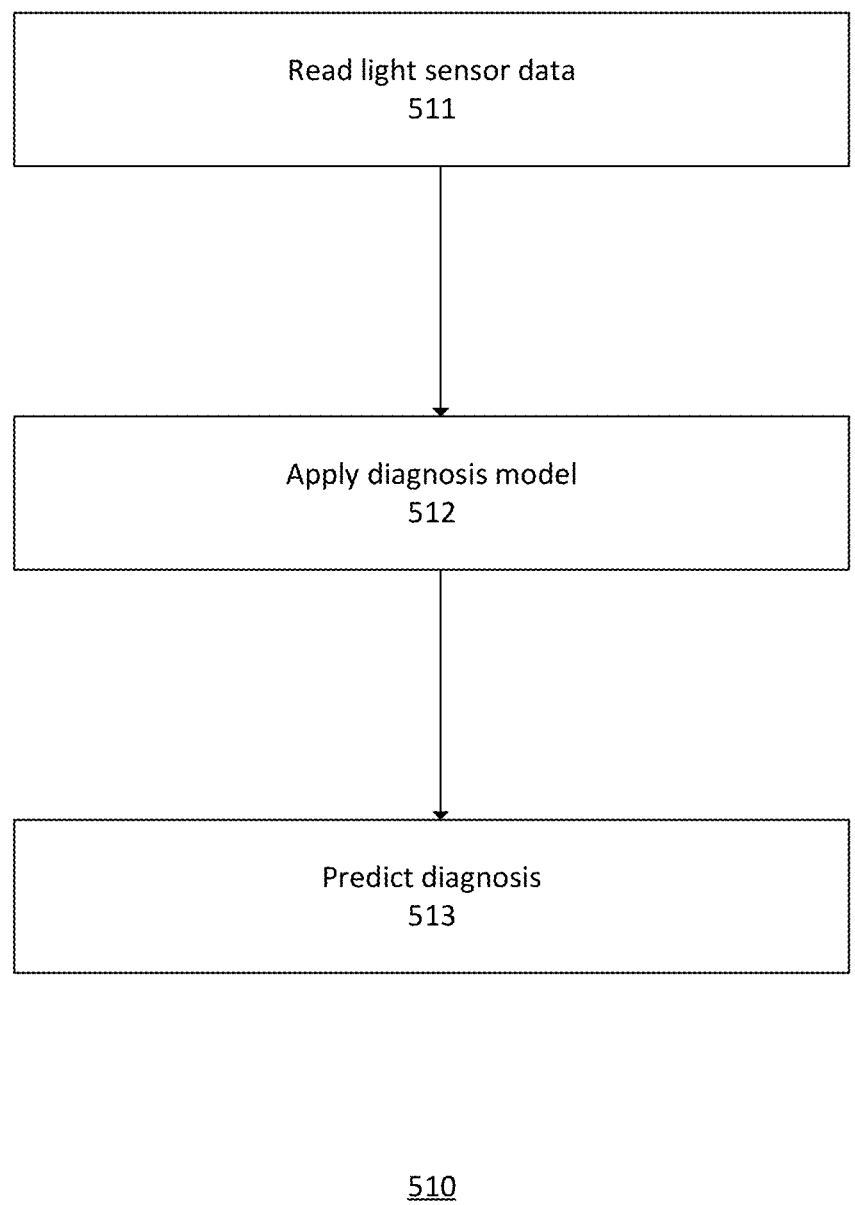
FIG. 5B illustrates an exemplary method for performing diagnosis.

FIG. 5B illustrates an exemplary method 510 perform diagnosis. In step 511, the portable reader 410 reads light sensor data from an inserted strip. Step 511 may occur identically, or similarly, to step 501. In some embodiments, the light sensor data is read only once in step 501 and the reading is reused in step 511.

In step 512, the light sensor data may be input into the diagnosis model. The diagnosis model may analyze the light sensor data to determine the presence or absence of a disease state or other abnormal state. In one embodiment, the diagnosis model is a classification model. The diagnosis model may output a binary result of "healthy" or "unhealthy." The unhealthy condition may be detected as a result of the analytes being too low (below a threshold) or too high (above a threshold) as indicated by the colors of the strip represented by the light sensor data. The diagnosis model may also include multiple states such as "healthy," "warning," and "unhealthy." The diagnosis model may be trained to detect these conditions by inputting training examples and target outputs for the training examples. The diagnosis model may therefore learn an association between light sensor data and the associated healthy or unhealthy states.

For example, states that may be recognized by the diagnosis model may include, for example, diabetes, ketosis, cancer, blood clotting, and so on.

In step 513, the diagnosis model may output a prediction of a healthy state or an unhealthy or abnormal state. The output may be a series of probabilities of the existence of each state. The state with highest probability may be selected as the predicted state. In addition, the diagnosis model may also output a confidence value that identifies the confidence with which it is making its prediction.

In an embodiment, when an unhealthy or abnormal state is detected, the system continues to application of the measurement model 413 using method 520, and if a health state is detected, then the system stops. However, in other embodiments, the system continues to application of the measurement model (method 520) regardless of whether the diagnosis was a healthy or unhealthy state.

Figure 5C:
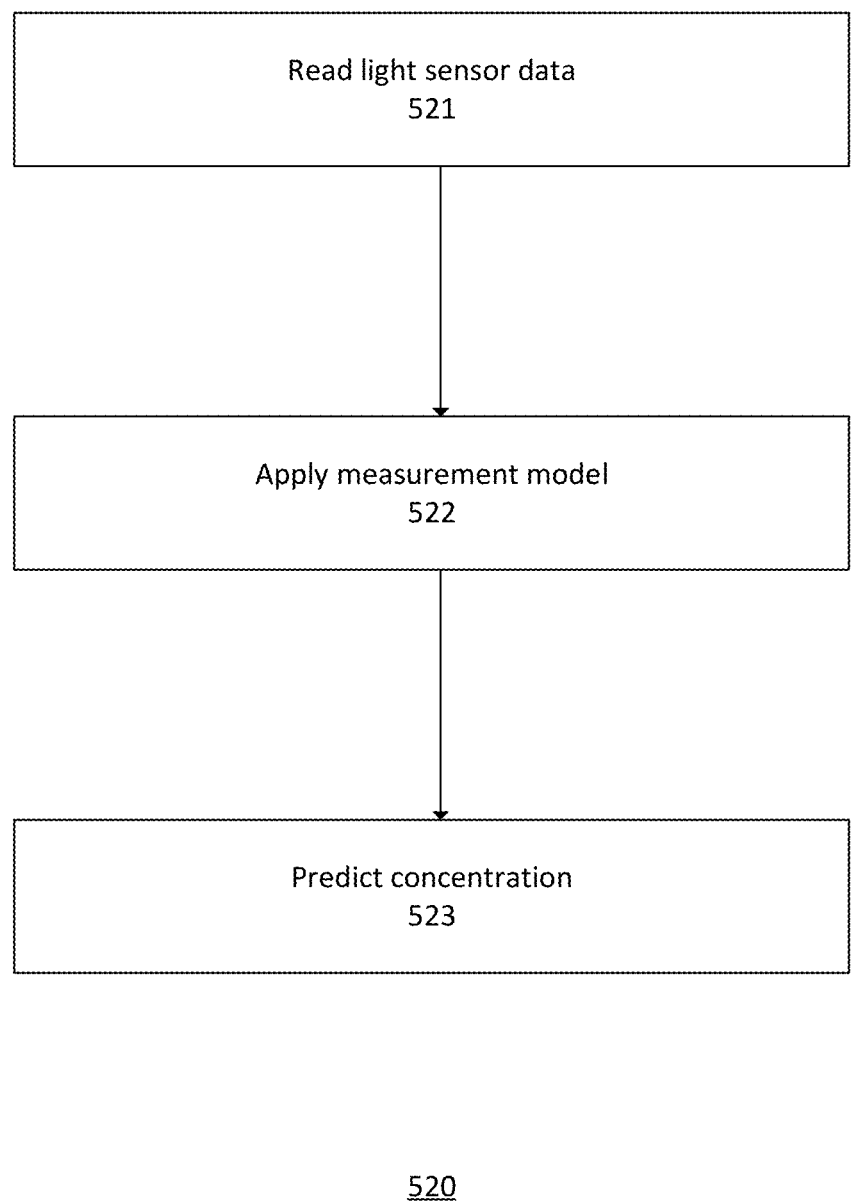
FIG. 5C illustrates an exemplary method for performing measurement.

FIG. 5C illustrates an exemplary method 520 perform measurement. In step 521, the portable reader 410 reads light sensor data from an inserted strip. Step 521 may occur identically, or similarly, to step 501. In some embodiments, the light sensor data is read only once in step 501 and the reading is reused in step 521.

In step 522, the light sensor data may be input into the measurement model. The measurement model may analyze the light sensor data to measure the concentration of an analyte. In one embodiment, the measurement model is a regression model. The measurement model may be trained to output a number representing the concentration of an analyte by inputting training examples and target outputs (concentration numbers) for the training examples. The measurement model may therefore learn an association between light sensor data and concentration values for an analyte. Concentrations may be learned in various units such as milligrams per mole, milligrams per liter, moles per liter, percentages, ratios, and so forth.

In step 523, the measurement model may output a prediction of a concentration value. The output may be a real or integral number representing concentration in various units. In addition, the measurement model may also output a confidence value that identifies the confidence with which it is making its prediction.

The outputs of the anomaly detection model 411, diagnosis model 412, and measurement model 413 may optionally be combined together and output to the user either separately or in combination.

What is claimed is:

1. A method for a reagent strips reader and smartphone to assess analytes in bodily fluids, comprising:
   measuring a light intensity of an inserted strip by a light sensor and storing it as light intensity data;
   transmitting the light intensity data to the smartphone;
   analyzing the light intensity data by an anomaly detection model to detect the presence of anomalies;
   based on a predicted anomaly output of the anomaly detection model indicating a correct operation of light intensity measurement by the light sensor determining a presence of a healthy state or an unhealthy state by analyzing by a diagnosis model a relationship between one or more colors represented in the light intensity data and a threshold value;
   based on a determination of the presence of the unhealthy state, analyzing the light intensity data by a measurement model to predict a concentration amount of an analyte indicated according to one or more learned associations between colors represented in the light intensity data and analyte concentration values; and
   displaying one or more results from the diagnosis model and measurement model to a user.

2. The method of claim 1, wherein the anomaly detection model comprises a classification model.

3. The method of claim 1, wherein the diagnosis model comprises a binary classification model.

4. The method of claim 1, wherein the measurement model comprises a regression model.

5. The method of claim 1, wherein the diagnosis model comprises a diagnosis model for
   detecting the presence of diabetes.

6. The method of claim 1, wherein the diagnosis model comprises a diagnosis model for detecting the presence of ketosis.

7. The method of claim 1, wherein the anomaly detection model is configured to detect
   the presence or absence of the strip.

8. The method of claim 1, wherein the anomaly detection model, diagnosis model, and measurement model are components of an ensemble learning system.

9. The method of claim 1, wherein the light intensity data comprises RGB values.

* * * * *